United States Patent [19]

Heilmann et al.

[11] Patent Number: 4,906,792

[45] Date of Patent: Mar. 6, 1990

[54] O-HYDROXYALKYLATION OF 1,1-DIHYDROPERFLUORINATED ALCOHOLS

[75] Inventors: Steven M. Heilmann; Larry R. Krepski; Dean M. Moren; Jerald K. Rasmussen, all of St. Paul, Minn.

[73] Assignee: Minnesota Mining and Manufacturing Company, St. Paul, Minn.

[21] Appl. No.: 267,035

[22] Filed: Nov. 4, 1988

[51] Int. Cl.$^4$ ............................................. C07C 31/36
[52] U.S. Cl. ..................................................... 568/812
[58] Field of Search ......................................... 568/812

[56] References Cited

U.S. PATENT DOCUMENTS 3,394,115  7/1968  Sorkin ................................. 260/80.9
3,532,674  10/1970  Banitt ................................. 260/78.4

FOREIGN PATENT DOCUMENTS 482433  4/1976  U.S.S.R. ............................. 568/812

Primary Examiner—Werren B. Lone
Attorney, Agent, or Firm—Donald M. Sell; Walter N. Kirn; Lorraine R. Sherman

[57] ABSTRACT

Mono O-hydroxyalkylated derivatives of 1,1-dihydroperfluorinated alcohols are prepared by reaction the alcohols with alkylene carbonates. The O-hydroxyalkylated derivatives are useful non-ionic surfactants and emulsifiable compounds for fire extinguishing systems.

15 Claims, No Drawings

O-HYDROXYALKYLATION OF 1,1-DIHYDROPERFLUORINATED ALCOHOLS

FIELD OF THE INVENTION

This invention relates to a novel process for preparing O-hydroxyalkylated derivatives of 1,1-dihydroperfluorinated alcohols. The O-hydroxyalkylated derivatives are useful as non-ionic surfactants and emulsifiable compounds for fire extinguishing systems.

BACKGROUND OF THE INVENTION

O-Hydroxyalkylation of 1,1-dihydroperfluorinated alcohols has most commonly been conducted using alkylene oxide reagents. U.S. Pat. No. 3,394,115, for example, teaches the O-hydroxyethylation of 2,2,2-trifluoroethanol using ethylene oxide. Despite employing a 1:1 stoichiometry of reactants, the monohydroxyethylated product was obtained in only 50 percent yield, with the simultaneous formation of the product resulting from addition of two molecules of ethylene oxide in 25 percent yield. The problem of polyalkylation was circumvented somewhat in U.S. Pat. No. 3,532,674 (Example 1, Method B). By adding two-thirds of an equivalent of ethylene oxide slowly over the course of several hours per equivalent of 1,1-dihydroperfluorinated alcohol, a reasonably good selectivity to the monohydroxyethylated product was achieved. The conversion (based on starting alcohol), however, was not indicated and, even so, the theoretical yield could only be 67 percent. The problem with alkylene oxides, aside from their toxicity and well-known explosion potential, is that they do not discriminate well between starting and product alcohols.

Alkylene carbonates are stable, relatively inexpensive, non-toxic, and non-gaseous (at room temperature and pressure) compounds. They have been utilized to provide O-hydroxyalkylated phenols (cf. T. Yoshino, et al., Bull.-Chem. Soc. Japan, 46, 553 (1973)) and perfluoroalkanesulfonamides (cf. H. Niederpruem, et al., Liebigs Ann. Chem, 11 (1973)). No reports exist of alkylation of 1,1-dihydroperfluorinated alcohols using alkylene carbonates.

In related work, ethylene sulfite has been utilized to provide O-hydroxyethylated 1,1-dihydroperfluorinated alcohols (cf. SU 482,433 (1976)). Aside from the increased cost of the reagent, emission of the extremely acidic sulfur dioxide by-product can lead to significant processing and pollution problems.

SUMMARY OF THE INVENTION

The present invention provides an improved process for the mono O-hydroxyalkylation of 1,1-dihydroperfluorinated alcohols.

Briefly, the present invention involves reacting 1,1-dihydroperfluorinated alcohols with an alkylene carbonate in the presence of a catalyst. Alkylene carbonates react principally with 1,1-dihydroperfluorinated alcohols and not with the O-hydroxyalkylated alcohol products, thereby affording a high selectivity towards monoalkylation.

The process of the present invention provides monoether products almost exclusively, in contrast to other known methods which yield significant amounts of polyether by-products.

The O-hydroxyalkylated derivatives are useful as non-ionic surfactants and emulsifiable compounds for fire extinguishing systems. Additionally, the O-hydroxyalkylated derivatives are useful synthetic intermediates to esters which are more hydrolytically stable, are less prone to crystallize, and are often more thermally stable than esters derived from the starting 1,1-dihydroperfluorinated alcohols.

In this application:

"alkyl" and "alkylene" mean the monovalent and divalent residues remaining after removal of one and two hydrogen atoms, respectively, from a linear or branched chain hydrocarbon having 1 to 20 carbon atoms;

"lower" alkyl means C-1 to C-4 alkyl;

"aryl" means the monovalent residue remaining after removal of a hydrogen atom from an aromatic compound (single ring and multi- and fused-cyclic) having 5 to 12 ring atoms and includes substituted aromatics such as lower alkaryl and aralkyl, lower alkoxy, N,N-di(-lower alkyl)amino, nitro, cyano, halo, and lower alkyl carboxylic acid ester, wherein "lower" means C-1 to C-4;

"cycloalkyl" means the monovalent residue remaining after removal of a hydrogen atom from a saturated cyclic hydrocarbon having 3 to 12 carbon atoms;

"essentially pure" means greater than 90 weight percent;

"substantially perfluorinated" means hydrocarbon groups in which at least 50 percent of the hydrogen atoms have been replaced by fluorine; and "crown ether" means a cation complexing, salt solubilizing additive such as 18-crown-6 (Formula A), tris(3,6-dioxaheptyl)amine (Formula B), and a linear polyethylene glycol compound such as $HOCH_2CH_2(OCH_2CH_2)_2{}_5OCH_2CH_2OH$.

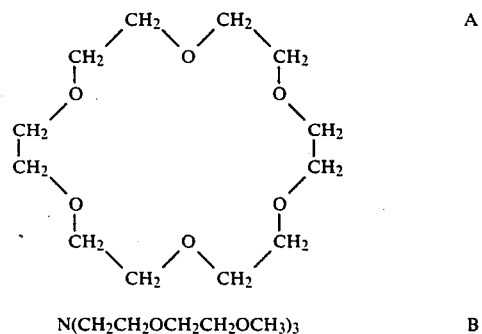

A

B

DESCRIPTION OF THE INVENTION

This invention provides a method for the preparation of essentially pure mono O-hydroxyalkylated 1,1-dihydroperfluorinated alcohols, the method being accomplished by reaction of a 1,1-dihydroperfluorinated alcohol of Formula I:

$$\underset{(HOCH)_a R_F}{\overset{R^1}{|}} \quad \text{I}$$

wherein
$R^1$ is hydrogen or lower alkyl;
a is 1 or 2; and
$R_F$ is a substantially perfluorinated alkyl, cycloalkyl, or aryl group when a is 1, and substantially perfluorinated alkylene when a is 2, with an alkylene carbonate of Formula II:

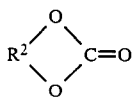

wherein $R^2$ is an alkylene group having 2 to 4 carbon atoms, in the presence of an effective amount of a catalyst to produce an O-hydroxyalkylated compound having Formula III:

wherein $R^1$, $R^2$, a, and $R_F$ are as defined above.

Many of the 1,1-dihydroperfluorinated alcohols of Formula I useful in the invention are commercially available. These include 2,2,2-trifluoroethanol; 2,2,3,3-tetrafluoro-1,4-butanediol; 1H,1H,3H-tetrafluoro-1-propanol; 3,3,4,4,4-pentafluoro-2-butanol; 1H,1H-pentafluoro-1-propanol; 2,2,3,3,4,4-hexafluoro-1,5-pentanediol; 1,1,1,3,3,3-hexafluoro-2-propanol; 1H,1H-heptafluoro-1-butanol; 1,1,1,2,2,3,3-heptafluoro-4-octanol; 3,3,4,4,5,5,5-heptafluoro-2-pentanol; 3,3,4,4,5,5,6,6-octafluoro-2-heptanol; 1H,1H,6H,6H-octafluorohexanediol; 1H,1H,5H-octafluoro-1-pentanol; 2,2,3,3,4,4,5,5,6,6-decafluoro-1-methylheptan-1-ol; undecafluorocyclohexylmethanol; 1H,1H,7H-dodecafluoro-1-heptanol; 1H,1H-pentadecafluorooctan-1-ol; 1H,1H,9H-hexadecafluoro-1-nonanol; and 1H,1H,11H-eicosafluoro-1-undecanol.

Suitable alkylene carbonates of Formula II include ethylene carbonate, propylene carbonate, and 1,3-dioxan-2-one, with ethylene carbonate being preferred.

Suitable catalysts for the process are salts containing basic anions such as carbonate, acetate, and propionate or nucleophilic anions such as iodide and bromide which are capable of generating a basic carbonate, vide infra. The nature of the cation is also important to facilitate solubility in the perfluorinated alcohol-alkylene carbonate medium. Useful solubilizing cations include tetraalkylammonium, tetraalkylphosphonium, and cesium ions. With lithium, sodium, and potassium ions it may be necessary to employ a crown ether additive such as tris(3,6-dioxaheptyl)amine, 15-crown-5, or 18-crown-6 in order to provide an effective catalyst (these compounds are commercially available). Useful catalysts include tetramethylammonium iodide, tetrabutylammonium iodide, cesium acetate, and potassium carbonate (with 18-crown-6).

The reaction is most efficiently conducted by mixing the 1,1-dihydroperfluorinated alcohol; 1.25–5.00 equivalents (based on the alcohol), preferably 1.50–2.00 equivalents, of the alkylene carbonate; and 1.00–10.00 weight percent (based on alcohol), preferably 2.00–5.00 wt. percent of the catalyst. The mixture is then warmed at 100° to 190° C., more preferably 120° to 140° C., until gas, i.e., carbon dioxide, evolution ceases. The reaction mixture is then cooled to room temperature, washed with water to remove excess alkylene carbonate and catalyst, dried, and vacuum distilled to obtain the pure O-hydroxyalkylated product.

While not wishing to be bound by any reaction mechanism or explanation, it is felt that the increased acidity, about 1000 times greater, of 1,1-dihydroperfluorinated alcohols compared to other alcohols accounts for the remarkable selectivity towards mono O-hydroxyalkylation per hydroxy unit in the 1,1-dihydroperfluorinated alcohol. The alkylene carbonate reagents are believed to alkylate by the mechanism shown in the following chemical equations in which ethylene carbonate, 2,2,2-trifluoroethanol (TFE), and a nucleophilic iodide catalyst are employed.

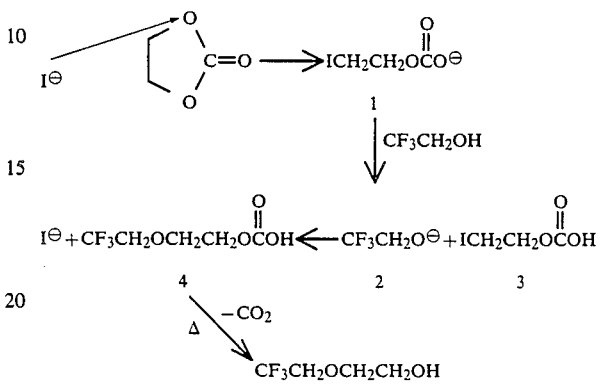

In the chemical equations the iodide catalyst first attacks the ethylene carbonate to generate the basic carbonate intermediate (1) which further generates the conjugate base of TFE (2). Intermediates 2 and 3 engage in a substitution of TFE (2) for iodide to form 4 which is thermally unstable and loses carbon dioxide yielding the mono O-hydroxyethylated end product, 2,2,2-trifluoroethyl 2'-hydroxyethyl ether.

If the O-hydroxyalkylated products are further alkylated at all in the process, it probably derives from alkylene oxide formation from the alkylene carbonate. This takes place slowly at the above specified reaction temperatures but occurs at appreciable rates at temperatures above 160° C. (for the preferred ethylene carbonate).

The mono O-hydroxyalkylated 1,1-dihydroperfluorinated alcohol products of the invention possess both hydrophobic ($R_F$) and hydrophilic (O—$R^2$—OH) regions and are potent surface active agents. Therefore, they find utility as non-ionic surfactants in a variety of applications including fire extinguishing systems because of their ability to float water on top of gasoline and organic liquids. Furthermore, the O-hydroxyalkylated products are useful reactants for synthesizing carboxylic acid esters. Because the less acidic O-hydroxyalkylated alcohol products make poorer leaving groups in hydrolysis reactions, these ester products are more hydrolytically stable then those derived from 1,1-dihydroperfluorinated alcohols. Another benefit is that incorporation of the ether group provides a "swivel" action to the ester group which inhibits crystallization. This is especially useful in acrylate or acrylamidoacylated ester monomer products and their utilization in UV curing situations which are most preferably performed in the absence of solvents.

Objects and advantages of this invention are further illustrated by the following examples, but the particular materials and amounts thereof recited in these examples, as well as other conditions and details, should not be construed to unduly limit this invention.

EXAMPLE 1

Preparation of 1,1-Dihydroperfluorooctyl 2-Hydroxyethyl Ether

In a three liter, round-bottomed flask equipped with a mechanical stirrer, thermometer, and condenser/gas bubbler arrangement were charged 1,1-dihydroperfluoro-1-octanol (DHPFO) (available from 3M, St. Paul, MN) (2326 grams; 5.815 moles), ethylene carbonate (available from Jefferson Chemical Co., Bellaire, TX) (768 grams; 8.72 moles), and tetramethylammonium iodide (available from Aldrich Chemical Co., Milwaukee, WI) (23.3 grams; 0.116 mole). The mixture of solids was warmed to about 90° C. to achieve a homogeneous light brown solution. Warming was continued, and the color of the reaction mixture lightened noticeably at 110° C. At 115° C. gas evolution was observed, and the temperature was slowly raised to 140° C. over the next few hours so that gas evolution did not become uncontrollably fast.

Gas evolution continued for about 48 hours, at which point gas liquid phase chromatography (glpc) analysis showed that less than 5 percent of the starting alcohol remained, about 90 percent of one higher boiling component was present, with only about 5 percent of a still higher boiling component (presumably dialkylated material) being detected. The reaction mixture was cooled and poured into a separatory funnel containing 2400 mL of ether and 2400 mL of water. The organic layer was dried over anhydrous magnesium sulfate, and the ether was removed using a rotary evaporator. The residue was vacuum fractionally distilled.

Material distilling at 65°–66° C./0.7 Torr. was collected and was analyzed to be greater than 97 percent pure by glpc. The structure of the title compound was corroborated by IR, $^1$H-NMR, and $^{13}$C-NMR spectroscopy. The fraction weighed 1761 grams which represented a 68 percent yield based on starting alcohol.

EXAMPLES 2–9

The following examples examine the efficiencies of various catalysts and reaction conditions as well as demonstrate the desirability of employing a stoichiometric excess of the alkylene carbonate reagent Percent conversions were determined by glpc.

| Example | DHPFO (mmole) | Ethylene Carbonate (mmole) | Catalyst (mmole) | Reaction Condition | % Conv. |
|---|---|---|---|---|---|
| 2 | 52 | 55 | Bu$_4$NI[b] (1.0) | 3 h[a], 155° C. | 61 |
| 3 | 52 | 55 | Bu$_4$NI (1.0) | 3 h, 140° C. | 40 |
| 4 | 52 | 55 | NaI (5.0) *TDA (5.0) | 5 h, 140° C. | 62 |
| 5 | 52 | 52 | Bu$_4$NI (1.0) | 24 h, 147° C. | 79 |
| 6 | 52 | 78 | Bu$_4$NI (1.0) | 24 h, 147° C. | 96 |
| 7 | 52 | 104 | Bu$_4$NI (1.0) | 24 h, 147° C. | 99 |
| 8 | 25 | 37.5 | NaI (0.5) | 20 h, 140° C. | **tr. |
| 9 | 25 | 37.5 | LiI (1.0) | 23.5 h, 140° C. | 56 |

*TDA means tris(3,6-dioxaheptyl)amine available from Rhone-Poulenc Inc., Monmouth Junction, NJ.
**tr. means trace hours
[a]h means hours
[b]Bu$_4$NI means tetrabutylammonium iodide

EXAMPLE 10

Preparation of 1,1-Dihydroperfluorooctyl 2-Hydroxy-2-methylethyl Ether

A 250 mL round-bottomed flask equipped with a magnetic stirring bar and condenser/gas bubbler arrangement was contained in a heating oil bath. The flask was charged with DHPFO (63.83 grams; 0.159 mole), propylene carbonate (available from Aldrich Chemical Co., Milwaukee, WI) (24.4 grams; 0.239 mole), and tetramethylammonium iodide (0.64 gram; 0.0032 mole), and the mixture was heated to 160° C. before any gas evolution was observed. The propylene carbonate reagent required more forceful conditions than ethylene carbonate in Example 1; also, conversion to propylene oxide was a more significant side reaction. In order to achieve an 80% conversion of starting alcohol, an additional 40.5 grams (0.40 mole) of propylene carbonate were added and reaction temperatures of between 170°–180° C. were required for a total of 52 hours. The reaction mixture was worked up as in Example 1. Fractional distillation provided 33.1 grams of the title compound distilling at 50° C./0.4 Torr. This amounted to an overall yield of 45 percent (or 57 percent based on converted starting alcohol). The IR, $^1$H-NMR, and $^{13}$C-NMR corroborated the title structure.

Various modifications and alterations of this invention will become apparent to those skilled in the art without departing from the scope and spirit of this invention, and it should be understood that this invention is not to be unduly limited to the illustrative embodiments set forth herein.

We claim:

1. A process comprising the steps:
   a) reacting
   (1) a 1,1-dihydroperfluorinated alcohol having the formula

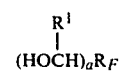

I wherein
   $R^1$ is hydrogen or lower alkyl;
   a is 1 or 2 ; and
   $R_F$ is a substantially perfluorinated alkyl, cycloalkyl, or aryl group when a is 1, and perfluorinated alkylene when a is 2; with
   (2) an alkylene carbonate having the formula

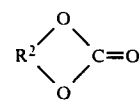

II wherein $R_2$ is an alkylene group having 2 to 4 carbon atoms;

(3) in the presence of an effective amount of a catalyst, wherein said catalyst is a salt containing a basic anion or a nucleophilic anion, and a solubilizing cation; and b) isolating the resulting O-hydroxyalkylated derivative of said 1,1-dihydroperfluorinated alcohol having the formula

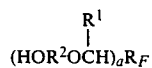   III wherein $R^1$, $R^2$, a, and $R_F$ are as defined above.

2. The process according to claim 1 wherein said 1,1-dihydroperfluorinated alcohols are selected from the group consisting of 2,2,2-trifluoroethanol; 2,2,3,3-tetrafluoro-1,4-butanediol; 1H,1H,3H-tetrafluoro-1-propanol; 3,3,4,4,4-pentafluoro-2-butanol; 1H,1H-pentafluoro-1-propanol; 2,2,3,3,4,4-hexafluoro-1,5-pentanediol; 1,1,1,3,3,3-hexafluoro-2-propanol; 1H,1H-heptafluoro-1-butanol; 1,1,1,2,2,3,3-heptafluoro-4-octanol; 3,3,4,4,5,5,5-heptafluoro-2-pentanol; 3,3,4,4,5,5,6,6-octafluoro-2-heptanol; 1H,1H,6H,6H-octafluorohexanediol; 1H,1H,5H-octafluoro-1-pentanol; 2,2,3,3,4,4,5,5,6,6-decafluoro-1-methylheptan-1-ol; undecafluorocyclohexylmethanol; 1H,1H,7H-dodecafluoro-1-heptanol; 1H,1H-pentadecafluorooctan-1-ol; 1H,1H,9H-hexadecafluoro-1-nonanol; and 1H,1H,11H-eicosafluoro-1-undecanol.

3. The process according to claim 1 wherein said alcohol is 1,1-dihydroperfluoro-1-octanol.

4. The process according to claim 1 wherein said anion is selected from the group consisting of carbonate, acetate, propionate, iodide, and bromide.

5. The process according to claim 1 wherein said solubilizing cation is selected from the group consisting of tetraalkylammonium, tetraalkylphosphonium, and cesium ions.

6. The process according to claim 1 wherein said solubilizing cation is selected from the group consisting of lithium, sodium, and potassium ions.

7. The process according to claim 1 wherein said catalyst is selected from the group consisting of tetramethylammonium iodide, tetrabutylammonium iodide, cesium acetate, and potassium carbonate.

8. The process according to claim 6 wherein said reaction mixture further comprises a crown ether.

9. The process according to claim 8 wherein said crown ether is selected from the group consisting of tris(3,6-dioxaheptyl)amine or a 18-crown-6 ether.

10. The process according to claim 1 wherein said alkylene carbonate is present in the range of 1.25 to 5.00 equivalents based on the alcohol.

11. The process according to claim 1 wherein said alkylene carbonate is present in the range of 1.50 to 2.00 equivalents based on the alcohol.

12. The process according to claim 1 wherein said catalyst is present in the range of 1.00 to 10.00 weight percent based on the alcohol.

13. The process according to claim 1 wherein said catalyst is present in the range of 2.00 to 5.00 weight percent based on the alcohol.

14. The process according to claim 1 wherein said reaction mixture is heated at a temperature in the range of 100° to 190° C.

15. The process according to claim 1 wherein said alkylene carbonate is ethylene carbonate.

* * * * *

UNITED STATES PATENT AND TRADEMARK OFFICE
CERTIFICATE OF CORRECTION

PATENT NO. : 4,906,792

DATED : March 6, 1990

INVENTOR(S) : Steven M. Heilmann et al

It is certified that error appears in the above-identified patent and that said Letters Patent is hereby corrected as shown below:

Col. 1, line 7, kindly delete "dihvdroperfluorinated" and insert therefor -- dihydroperfluorinated --.

Col. 6, line 10, kindly delete "hours" and insert therefor -- amount --.

Signed and Sealed this

Third Day of March, 1992

Attest:

HARRY F. MANBECK, JR.

*Attesting Officer*  *Commissioner of Patents and Trademarks*